(12) United States Patent
Tai et al.

(10) Patent No.: US 6,534,295 B2
(45) Date of Patent: *Mar. 18, 2003

(54) CELL LYSIS DEVICE

(75) Inventors: Yu-Chong Tai, Pasadena, CA (US); Sang-Wook Lee, Fullerton, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/954,684

(22) Filed: Sep. 11, 2001

(65) Prior Publication Data

US 2002/0019035 A1 Feb. 14, 2002

Related U.S. Application Data

(63) Continuation of application No. 09/191,268, filed on Nov. 12, 1998, now Pat. No. 6,287,831.
(60) Provisional application No. 60/065,705, filed on Nov. 14, 1997.

(51) Int. Cl.[7] .................. C12N 13/00; C12M 1/33; C12M 3/08
(52) U.S. Cl. ................. 435/173.7; 435/173.1; 435/306.1; 204/194; 204/280; 204/600
(58) Field of Search ............. 435/173.7, 173.1, 435/306.1; 204/194, 280, 600

(56) References Cited

U.S. PATENT DOCUMENTS

| | | | |
|---|---|---|---|
| 4,778,769 A | * | 10/1988 | Forrest et al. |
| 4,971,910 A | * | 11/1990 | Zimmerman |
| 4,976,175 A | * | 12/1990 | Karube et al. |
| 5,491,097 A | * | 2/1996 | Ribi et al. |

* cited by examiner

*Primary Examiner*—Christopher R. Tate
(74) *Attorney, Agent, or Firm*—Fish & Richardson P.C.

(57) ABSTRACT

A micromachined cell lysis device with electrodes that are spaced by less than 10 μm from one another. The cells are attracted to the space between the electrodes and then lysed.

18 Claims, 4 Drawing Sheets

Oxidation

Cr-Au evaporation and pattern

Parylene C deposition and pattern

Packaging with glass channel

CELL LYSIS DEVICE

CROSS REFERENCE TO RELATED APPLICATION

This application is a continuation of U.S. application Ser. No. 09/191,268, filed Nov. 12, 1998, now U.S. Pat. No. 6,287,831 which claims the benefit of the U.S. Provisional Application No. 60/065,705, filed on Nov. 14, 1997, which are incorporated herein by reference.

STATEMENT AS TO FEDERALLY SPONSORED RESEARCH

The U.S. Government may have certain rights in this invention pursuant to Grant No. N66001-96-C-8632 awarded by the U.S. Navy.

BACKGROUND

It is known that an electrical field can be used to manipulate cells. Electrical manipulation of cells can be used for separating cells, holding cells, killing micro-organisms, or other operations.

Electrical manipulation of a cell is based on dielectrophoresis. A neutral particle, such as a microbial cell, will become polarized when subjected to a non-uniform electric field. Due to the non-uniformity of the field, a net force will act on the particle. This force will produce movement of the suspended cell. This phenomenon known as dielectrophoresis the inside of the cell has and holds a different charge than the outside of the cell.

Macro sized electroporation systems have been designed for injecting genes into cells. See. "Electroporation and Electrofusion in Cell Biology," E. Newman, A. E. Sauer, C. A. Jordan, ed. Plenum Press, New York, 1989. These systems often use electrical fields to make microsized pores on cell membranes.

Cell lysis typically refers to opening a cell membrane to allow the cell interior to come out. Cell lysing can be used to obtain intracellular material for further analysis such as DNA identification.

It is known to use the science of micromachining to manipulate cells. See, for example, S. Lee, "A Study of Fabrication and Applications of Micromachined Cell Manipulating Devices," Ph.D. Thesis, Seoul National University, pp. 77–81, 1996. However, no one has previously reported using micromachining to form a device for cell lysis. Usually, these systems use cuvets that have a few millimeter range electrode gap. Lysing cells with this kind of size requires a few kilovolts of voltage source across such a gap.

Prior cell lysing has been reported using pulsed electric fields in a macrosized electroporation system. See, for example, T. Grahl and H. Markl, "Killing of Microorganisms by Pulsed Electric Fields," *Appl. Microbio. Biotechnol.*, 45, pp. 148–157, 1996. The disadvantages of such a macrosized device have been described above.

J. Cheng, et al, "Preparation and Hybridization analysis of DNA/RNA from *E. Coli* on Microfabriacted Bioelectronic Chips" has suggested electronic cell lysis on a chip. However, this system still required hundreds of volts for lysing the cell.

SUMMARY

The present disclosure describes a new micromachined cell lysis device. A microsized cell lysis device as disclosed reduces the size of the entire system including the power source, since the electrode gap could be reduced to a few $\mu$m or smaller. This micro-sized cell lysis device is capable of operating on a small number of cells due to its small size.

A special way of using the electric field that can greatly simplify the purification steps is described. This can be used to prepare biosamples. In addition, the small size allows a reduction in voltage required for lysing. The voltage can be reduced to practical levels, e.g., less than 50 volts, since the electrode gap is on the order of microns.

A new structure is also described for cell lysis.

BRIEF DESCRIPTION OF THE DRAWING

These and other advantages will now be described in detail with respect to the accompanying drawings, wherein.

DESCRIPTION OF THE PREFERRED EMBODIMENTS

Figure 1A:
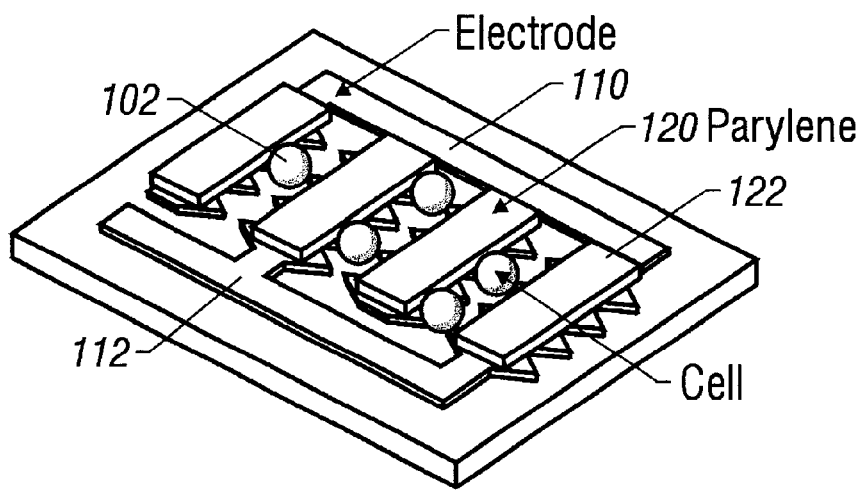
FIG. 1A shows a schematic view of the overall cell lysis device.
Figure 1B:
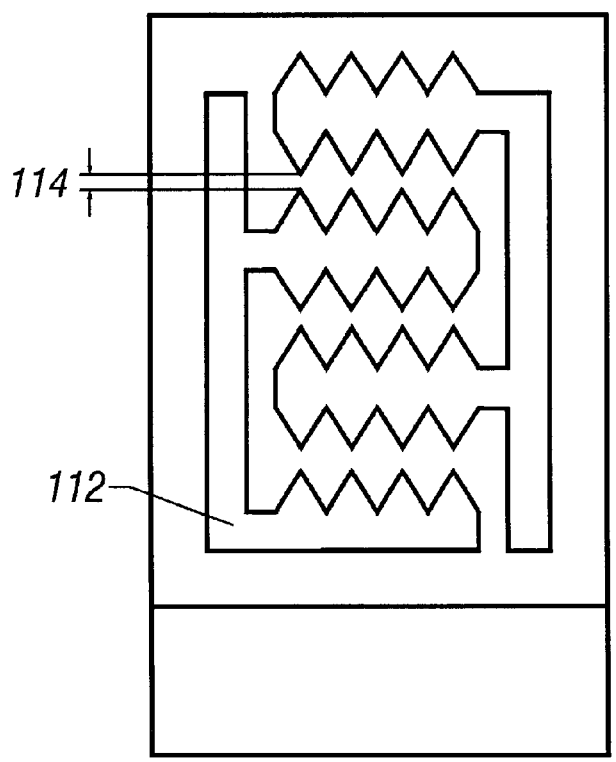
FIG. 1B shows a top view of the cell lysis electrode.

The basic lysis device is shown in plan view in FIGS. 1A and 1B. The device is made according to the fabrication steps explained below with reference to FIGS. 2A–2D.

The micromachining operates to form features on a silicon substrate.

Figure 2A:
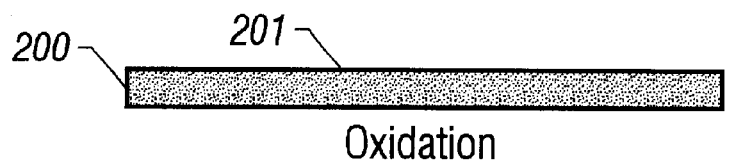
FIGS. 2A–2D show the fabrication steps of the cell lysis device.
Figure 2B:
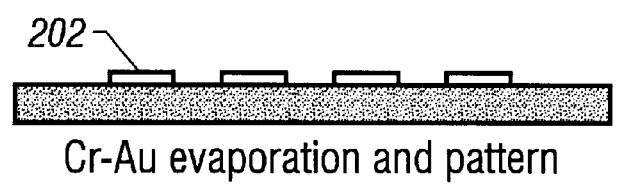

First an insulator is formed on the silicon substrate, by oxidizing the silicon substrate 200 to form a thermally-grown 5000 Å silicon oxide layer 201 as shown in FIG. 2A. Chromium/gold (Cr/Au) is thermally evaporated and patterned to form electrodes 202 on the oxidized surface. The electrodes are formed with a number of pointed portions facing one another, in the general shape shown in FIG. 1B.

Figure 2C:
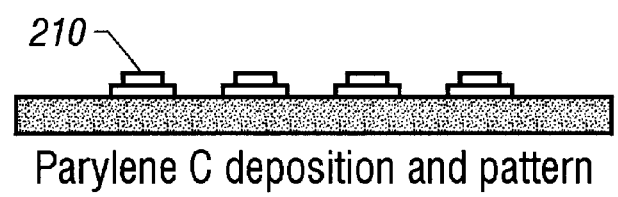

A 4 $\mu$m thick Parylene layer is deposited and patterned to form Parylene barriers 210 as shown in FIG. 2C. These barriers have side surfaces that hold the cell in a proper place, and form blocks between each pair of electrode surfaces.

Figure 2D:
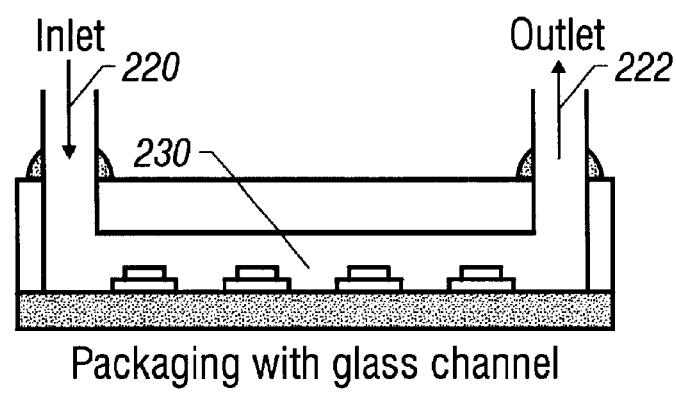

FIG. 2D shows bonding the thus-made assembly to a glass substrate which has an inlet 220, an outlet 222, and a channel is 230 between the inlet and outlet. The channel is 30 $\mu$m high, made by timed wet etching.

The preferred device is designed for yeast cells. The distance between electrodes is hence around 5 $\mu$m. More generally, the distance can range between about 0.8 $\mu$m and 100 $\mu$m (0.1 mm), more preferably on the order of e.g. 1–9.9 $\mu$m.

The final assembled device is shown in FIG. 1A. A number of cells are shown, such as cell 102. Cells are attracted by the dielectrophoretic force using an AC voltage. The cells are then lysed, using pulsed electric fields. The AC voltage depends on the conductivity and permitivity of the cell suspensions and the sizes of the cells. The cells are held between two electrodes 110, 112 and between the Parylene barriers 120, 122 for the lysing.

Any arrangement of pairs of electrodes, such as interdigitated or parallel, can be used for the cell lysing. Preferably, the edges of the electrodes are made sharp as shown in order to concentrate the field better on the cells. The nearest distance 114 between the two electrodes is preferably equal to the mean diameter of a cell plus the standard deviation of the cells in order to obtain the most effective lysing.

FIG. 1B hows a drawing of the electrode without the Parylene barriers present showing interdigitated electrodes. Distance 114 is defined as the distance between the sharp ends of the electrodes.

Figure 3:
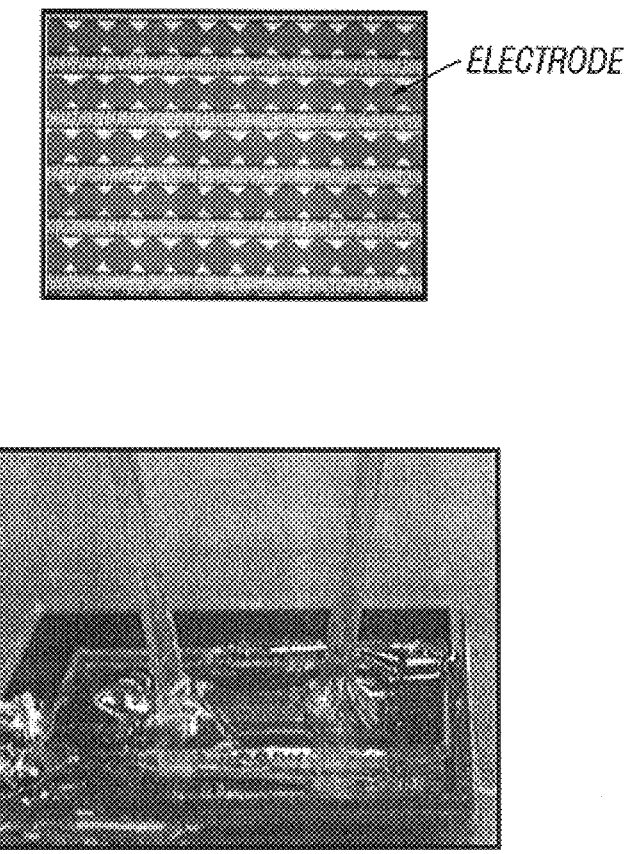
FIG. 3 shows a photograph of a fabricated device.

FIG. 3 shows a drawing of the device from the top, showing all the arrangements of the various structures.

Figure 4:
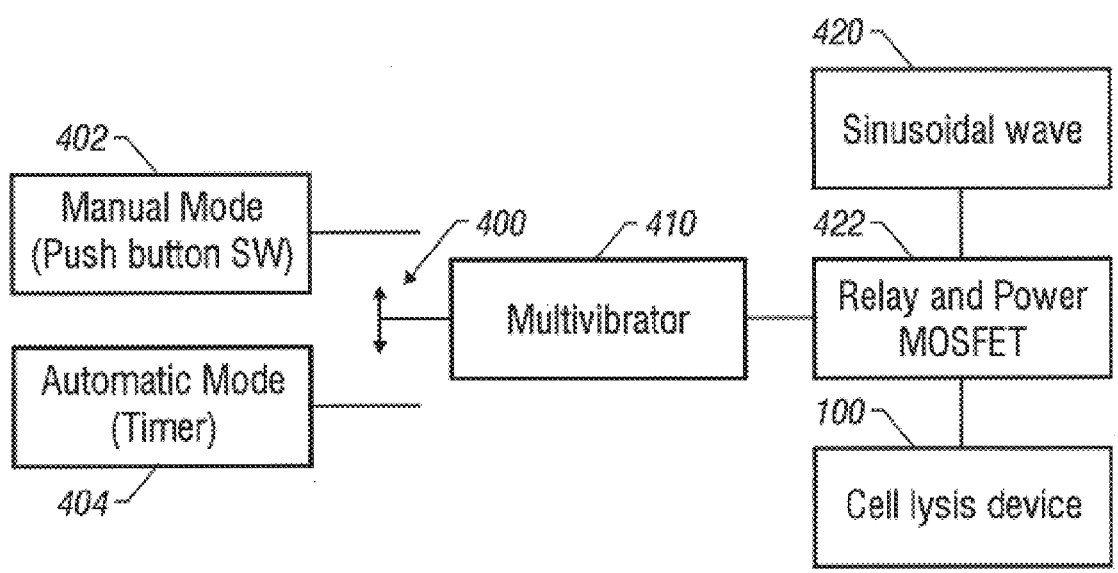
FIG. 4 shows schematically the power system used for cell lysis.

An important feature includes how the device is operated. A power system for the cell lysis is formed as shown in FIG. 4. Control is selected by a switch 400 which selects between manual mode or automatic mode. In the manual mode, the pulse is applied by a push-button switch 402. In the automatic mode, pulses are supplied at every defined interval. Pulse width control is provided by a multivibrator 410, typically a TTL-type multivibrator, part 74LS123. The switch 400 can be a single-pull, double-throw type relay.

A multipurpose function generator 420 provides the electric fields which attracts the cells. The electric field is preferably a sinusoidal wave. A power MOSFET 422 provides the output to the cell lysis device 100.

Figure 5:
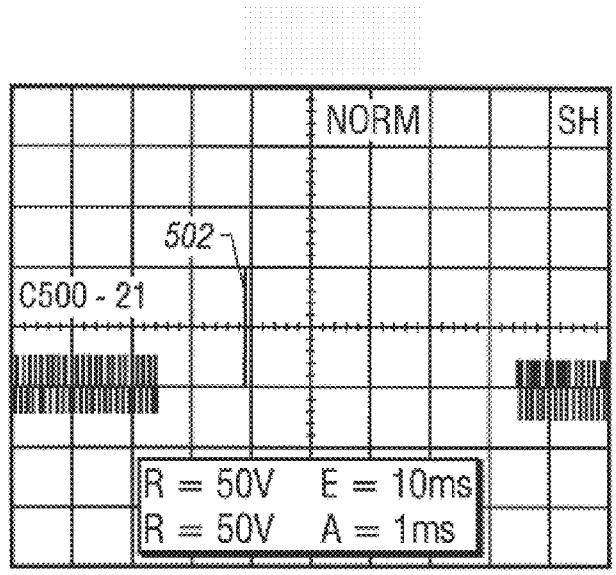
FIG. 5 shows a plot of a waveform for cell lysis.

A typical waveform is shown in FIG. 5, which shows a sample plot of the waveform for cell lysis. The waveform includes two parts—the attraction phase 500, and the lysing phase 502.

The attraction phase uses a 6 volt AC, 2 MHZ sample. This attracts the cells to the lysing locations. A sinusoidal wave is preferably used to attract the cell to the location. After a short delay, lysing pulse, a 100 $\mu$s, 20 volt pulse, is applied.

Figure 6:
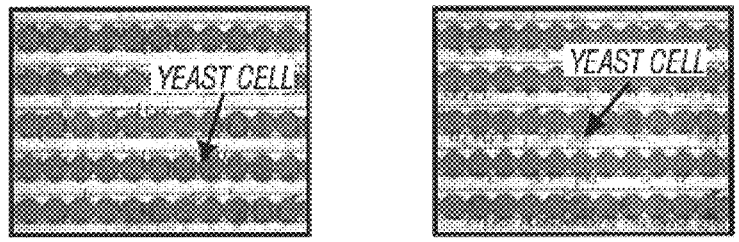
FIG. 6 shows drawings of yeast cells before and after lysing.

FIGS. 6A and 6B show the yeast cells before and after applying the pulsed voltage. FIG. 6A shows attraction of the yeast cells to the electrode when the 2 MHZ 6V AC voltage in FIG. 5 is applied. FIG. 6B shows the result of lysing. After lysing the cells, the inside and outside of the cells are electrically connected, and they will no longer attract to the electrodes by the AC voltage.

Figure 7:
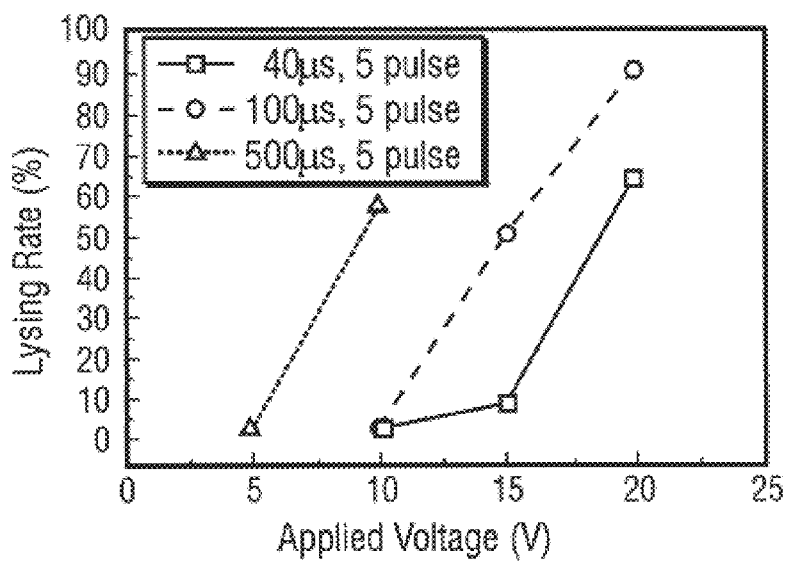
FIG. 7 shows a plot of lysis vs voltage.

FIG. 7 shows some representative lysing rates with different electric fields and pulse durations. The rate is increased with increased voltage and duration. Excessive pulse voltage and duration form electrolysis effects. The optimum value for yeast cell lysing is believed to occur at 100 $\mu$s and 20V. However, any voltage less than 50 volts is preferred and within the preferred embodiment.

Although only a few embodiments have been described in detail above, other embodiments are contemplated by the inventor and are intended to be encompassed within the following claims. In addition, other modifications are contemplated and are also intended to be covered. For example, other shapes and sizes of electrodes could be used. There could also be more than two electrodes. While the pointed electrodes are preferred, flat shaped electrodes can also be used.

What is claimed is:

1. A cell lysis apparatus, comprising:
   a substrate formed of a material that can be micromachined;
   an insulator, covering at least a portion of the substrate;
   a first electrode, formed on said insulator, and having a first area over which the first electrode forms a first sharp edge;
   a second electrode, also formed on said insulator, and having a second area, spaced from said first area, said second area forming a second sharp edge which is spaced from and facing said first sharp edge;
   a distance between said first and second sharp edges being less than 100 microns; and
   a power supply connection, enabling specified voltages to be applied between said first and second electrodes in a way which enables cell lysing.

2. An apparatus as in claim 1, further comprising a power supply, and a controller for said power supply, said power supply being controlled during the first time to dielectrophoretically attract cells to said first and second sharp edges, and being controlled during a second time, subsequent to said first time, to lyse attracted cells.

3. An apparatus as in claim 1, wherein said power supply is controlled during said first time with a lower voltage, and during said second time with a higher voltage.

4. An apparatus as in claim 1, wherein said first and second electrodes each include points thereon other than said first and second sharp edges, which points face one another.

5. An apparatus as in claim 1 wherein said substrate is formed of silicon.

6. An apparatus as in claim 1, further comprising a cell blocker element, between said first and second edges, and holding a cell to be lysed into a desired location.

7. An apparatus as in claim 6, wherein said cell blocker element is formed of Parylene.

8. An apparatus as in claim 1, further comprising an inlet, receiving cells to be lysed, and an outlet, outputting lysed cell material.

9. An apparatus as in claim 8, wherein each of said first and second areas extend in a first direction, and wherein a flow of cells from said inlet to said outlet extends in a direction perpendicular to said first direction.

10. A method of lysing, comprising:
    providing a first electrode with a first sharp-edged area and providing a second electrode with a second sharp edged area facing said first extended sharp edged area and separated therefrom by 100 microns or less, said area defining a cell holding area therebetween;
    first energizing said first and second electrodes with a first voltage less than 50 volts peak to peak and which is effective to attract cells into said area between said first and second electrode dielectrophoretically; and
    second energizing said first and second electrodes with a second voltage, greater than said first voltage, and which is effective to lyse said cells.

11. A method.as in claim 10, further comprising a blocker portion, holding said cells, said cell blocker element holding said cells between said first and second edges during said second energizing.

12. A method as in claim 10, wherein said first and second electrodes have specified edges which extend in a first direction, and further comprising flowing cells in a second direction perpendicular to said first direction.

13. A cell lysis apparatus, comprising:
    a substrate;
    an insulator, covering at least a portion of the substrate;
    a first array, comprising:
    a first electrode, formed on said insulator, and having a first area over which the electrode forms a first sharp edge;
    a second electrode, also formed on said insulator, and having a second area spaced from said first area, said second extended area forming a second sharp edge which is spaced from and facing said first sharp edge:

a distance between said first and second sharp edges being less than 100 microns, and a cell holding area being formed between said first and second sharp edges;

a second array, comprising:

a first electrode, formed on said insulator, and having a first area over which the first electrode forms a first sharp edge;

a second electrode, also formed on said insulator, and having a second area spaced from said first area, said second extended area forming a second sharp edge which is spaced from and facing said first sharp edge;

a distance between said first and second sharp edges being less than 100 microns, and a cell holding area being formed between said first and second sharp edges; and a power supply connection, enabling specified voltages to be applied between said first and second electrodes of each of said first and second array in a way which first enables attraction of cells and then enables lysing of cells which are attracted.

14. An apparatus as in claim 13, further comprising at least one cell blocking element, located between said first and second sharp edges to hold the cells at a specified location between said first and second sharp edges.

15. An apparatus as in claim 13, wherein said sharp edges are formed in the general shape of a zigzag.

16. An apparatus as in claim 13 wherein each of said first and second extended areas extend in a first direction, and further comprising a cell inlet and cell outlet positioned to cause said cells to move between said inlet and said outlet in a second direction perpendicular to said first-direction.

17. An apparatus as in claim 13, wherein said power supply uses a high frequency voltage pulse to attract said cells.

18. An apparatus as in claim 13, wherein said sharp edges each include a first portion extending in a first direction and a second portion extending in a second direction generally forming the shape of a zigzag.

* * * * *